(12) United States Patent
Lombardo et al.

(10) Patent No.: US 9,168,034 B2
(45) Date of Patent: Oct. 27, 2015

(54) SUTURE ANCHOR

(75) Inventors: Giuseppe Lombardo, New Port Richey, FL (US); Steven E. Fitts, Largo, FL (US); Peter C. Miller, Largo, FL (US)

(73) Assignee: Linvatec Corporation, Largo, FL (US)

( * ) Notice: Subject to any disclaimer, the term of this patent is extended or adjusted under 35 U.S.C. 154(b) by 767 days.

(21) Appl. No.: 12/756,554

(22) Filed: Apr. 8, 2010

(65) Prior Publication Data

US 2011/0224726 A1 Sep. 15, 2011

Related U.S. Application Data

(60) Provisional application No. 61/313,443, filed on Mar. 12, 2010.

(51) Int. Cl.
*A61B 17/04* (2006.01)
*A61B 19/00* (2006.01)

(52) U.S. Cl.
CPC .......... *A61B 17/0401* (2013.01); *A61B 17/0467* (2013.01); *A61B 2017/045* (2013.01); *A61B 2017/0409* (2013.01); *A61B 2017/0414* (2013.01); *A61B 2017/0432* (2013.01); *A61B 2017/0437* (2013.01); *A61B 2019/307* (2013.01)

(58) Field of Classification Search
CPC ........... A61B 17/0401; A61B 17/0467; A61B 17/04; A61B 2017/0409; A61B 2017/0432; A61B 2017/0437; A61B 2017/045; A61B 2017/0414; A61B 2019/307

USPC .......... 606/232, 139, 219, 224, 148, 228, 53, 606/144, 300; 623/13.14
See application file for complete search history.

(56) References Cited

U.S. PATENT DOCUMENTS

| | | | |
|---|---|---|---|
| 7,572,283 B1 * | 8/2009 | Meridew | 606/321 |
| 2004/0049207 A1 * | 3/2004 | Goldfarb et al. | 606/139 |
| 2006/0235413 A1 * | 10/2006 | Denham et al. | 606/72 |
| 2008/0097527 A1 * | 4/2008 | Lim et al. | 606/232 |
| 2008/0140118 A1 * | 6/2008 | Martinek | 606/232 |

* cited by examiner

*Primary Examiner* — Tuan V Nguyen
*Assistant Examiner* — Tin Nguyen
(74) *Attorney, Agent, or Firm* — Bond Schoeneck & King, PLLC

(57) ABSTRACT

There is described a suture anchor with anchor members moveable as between a suture-unlocked configuration and suture-locked configuration. In one embodiment, the anchor members include an outer anchor member with features, e.g., flexible barbs, configured to secure the suture anchor in the suture-locked configuration to material proximate a pre-formed hole in bone material. The outer anchor member is also configured with a bore to receive suture material, and which is sized and shaped to receive an inner anchor member therein. The inner anchor member includes securing features such as projections that compress the suture material against the surface of the bore when the suture anchor is actuated from the suture-unlocked configuration to the suture-locked configuration.

13 Claims, 16 Drawing Sheets

A-A

B-B

C-C

D-D

SUTURE ANCHOR

CROSS-REFERENCE TO RELATED APPLICATIONS

This application claims the benefit of priority under 35 U.S.C. §119(e) from U.S. Provisional Patent Application Ser. No. 61/313,443, entitled "Suture Anchor," filed on Mar. 12, 2010. The content of this application is incorporated by reference herein in its entirety.

TECHNICAL FIELD

The present invention is related to anchors for securing material to soft tissue and bone, and more particularly to embodiments of a knotless suture anchor.

BACKGROUND

Suture anchors are commonly employed during surgical procedures to secure soft tissue to bone. Such anchors are generally inserted into a pre-formed hole in the bone, so that a portion of filamentary material (e.g., suture material) extends out of the hole from the anchor. Suture material, as the term is used and described herein, include monofilament or multi-filament suture as well as any other metallic or non-metallic filamentary or wire-like material suitable for performing the function of a suture. This material can include both absorbable and non-absorbable materials.

For open and closed surgical procedures, the suture material is tied to the soft tissue in a manner that forms a knot. But for surgical procedures that are typically closed, including those procedures performed arthroscopically or endoscopically, the knot is often difficult to form. Suture anchors that do not require a knot, also referred to as "knotless suture anchors," have been developed to avoid the step of tying the knot.

One example of a knotless suture anchor is shown in U.S. Pat. No. 6,692,516 to West Jr. et al., assigned to the assignee hereof and incorporated by reference in its entirety herein. There is provided here an expandable metallic knotless suture anchor, which is difficult to implement in the form of non-metallic material. Another example is shown in U.S. Patent Application Publication No. 2005/0055052 filed by Lombardo et al., and assigned to the assignee hereof and incorporated by reference in its entirety herein. This application discloses a knotless suture anchor that is constructed of bio-absorbable material, but may be limited in its application to certain surgical procedures.

This limitation to certain surgical procedures is unfortunate because other procedures, including rotator cuff repairs, would benefit from knotless suture anchors, and more particularly, from a knotless suture anchor that is secured to the cancellous bone. It would be likewise beneficial if the knotless suture anchor is provided so as to prevent the tendency to migrate above the cortical layer of the bone, as well as from the level of the humeral head or other bone at the anchor site.

Therefore, there is a need for a knotless suture anchor that is compatible with a wide range of surgical procedures. There is likewise a need that the proposed knotless suture anchor is configured to engage not only the cancellous bone, but also to engage the bone in a manner that prevents migration of the anchoring device.

SUMMARY

The present invention relates generally to suture anchors for securing tissue to bone. Embodiments of the suture anchors described below provide features that improve fixation of the tissue by providing flexible barbs having a range of motion that prevents notching of the bone material.

BRIEF DESCRIPTION OF THE DRAWINGS

So that the manner in which the above recited features of the present invention can be understood in detail, a more particular description of the invention briefly summarized above, may be had by reference to the figures, some of which are illustrated and described in the accompanying appendix. It is to be noted, however, that the appended documents illustrate only typical embodiments of this invention and are therefore not to be considered limiting of its scope, for the invention may admit to other equally effective embodiments. Moreover, the drawings are not necessarily to scale, with emphasis generally being placed upon illustrating the principles of certain embodiments of invention.

Thus, for further understanding of the nature and objects of the invention, references can be made to the following detailed description, read in connection with the specification following below in which.

DETAILED DESCRIPTION

Illustrated in the appended drawings and discussed below are suture anchors, embodiments of which are configured to be deployed during surgical procedures such as those procedures that require securing soft tissue to bone. At a high level, suture anchors of the type described herein can include a pair of anchor members that are insertably engaged with one another to permit relative movement of the members as between a suture-locked configuration and a suture-unlocked configuration. When implemented in the surgical procedure (e.g., rotator cuff surgery), this relative movement is utilized to secure suture material in and to, e.g., the cancellous layer of the bone. Moreover, as will become apparent in the discussion that follows, suture anchors that incorporate concepts of the present invention are particularly beneficial because the length of the suture material in the suture anchor does not change as the relative position of the anchor members changes from the suture-unlocked configuration to the suture-locked configuration. Nor is the axis of compression of the suture material altered, a feature that maintains tension applied to the suture material during the surgical procedure at a substantially consistent level when actuating the anchoring device from its suture-unlocked configuration to suture-locked configuration in the bone.

Details of the construction of the anchor members for use in the suture anchor are provided below. It may be desirable that the anchor members can comprise biocompatible materials, which are sufficiently resilient and which permit the relative movement mentioned above. These materials may comprise compositions that are reabsorbed by the body, e.g., during the healing process of the bone. Exemplary materials that are suitable for use in the anchor members include, but are not limited to, polyetheretherketone ("PEEK"), polylactic acid/beta-tricalcium phosphate ("PLA/Beta-TCP") composites, ultra high molecular weight polyethylene ("UHM-WPE"), as well as other metallic, non-metallic, and polymeric materials. In some embodiments of the suture anchor, the materials that are selected for the anchor members may have physical properties that are consistent with, or compatible with certain performance factors for the suture anchor device. These performance factors may include, for example, tensile strength, shear strength, and flexibility of all or part of the suture anchor. Each of the performance factors mentioned above, and contemplated herein, may have values respecting both the configuration of the anchor members, as well as the changes in the suture anchor that may occur as the relative positions of the anchor members change in response to the movement from the suture-unlocked configuration to the suture-locked configuration.

Figure 1:
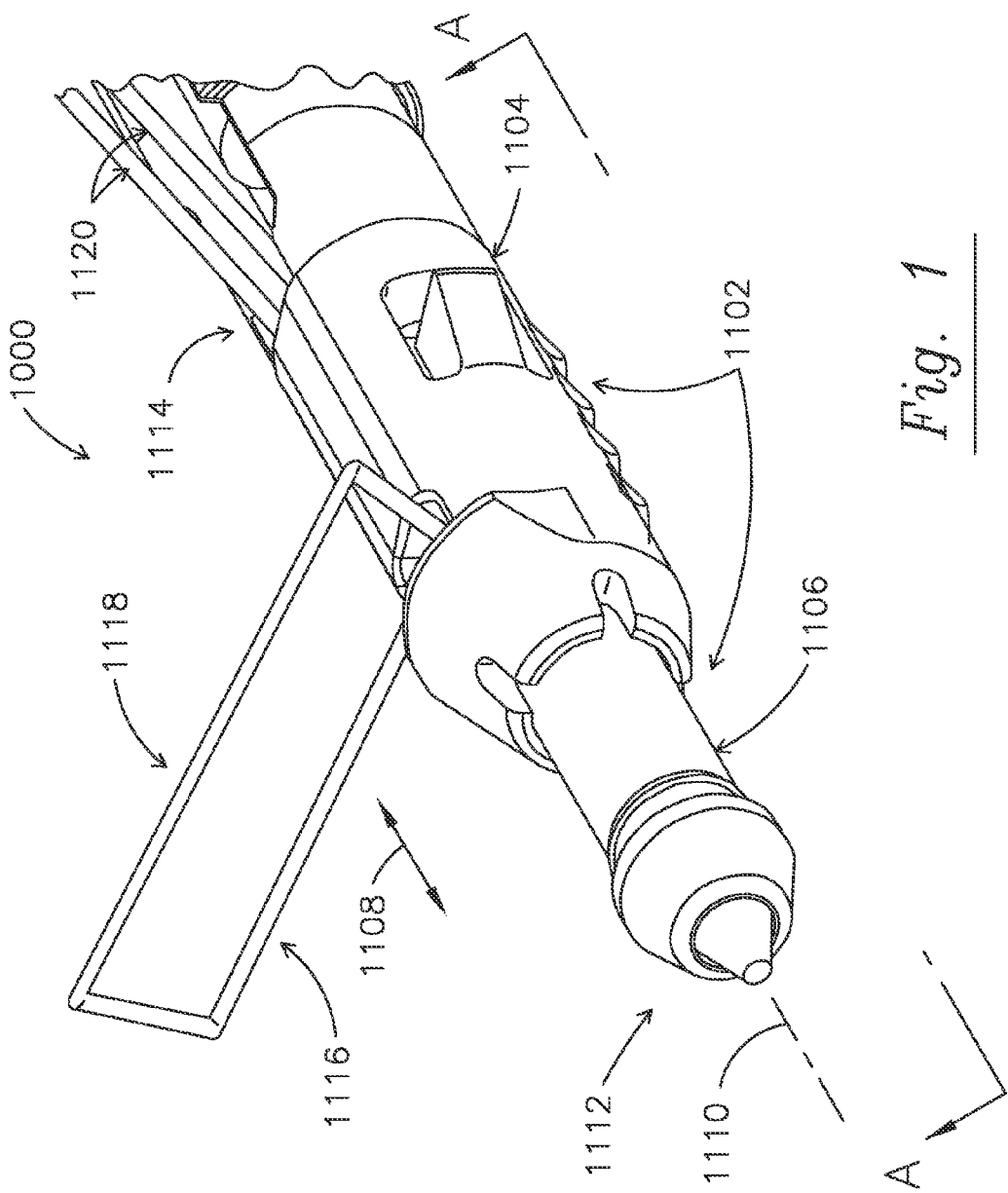
FIG. 1 is a top, perspective view of an exemplary embodiment of a suture anchor.
Figure 2:
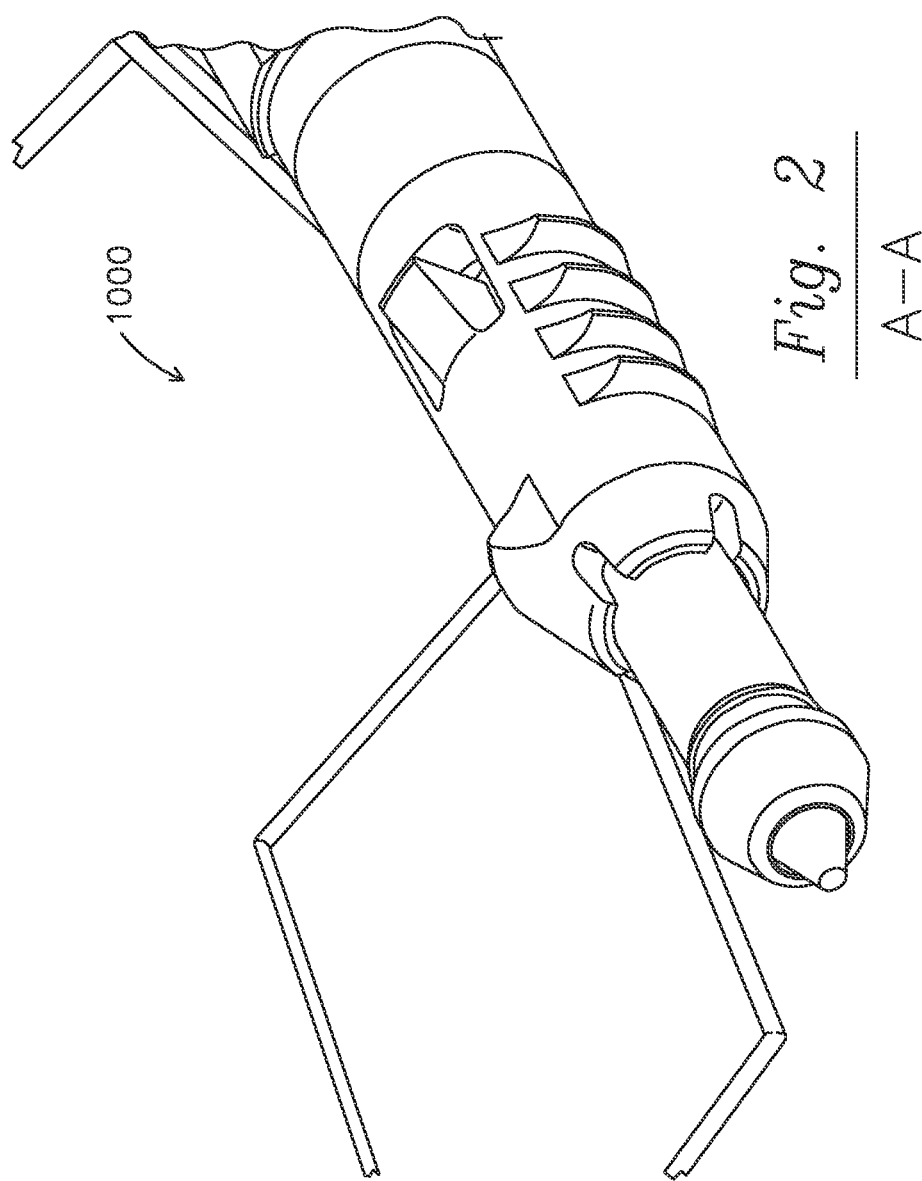
FIG. 2 is a side, perspective view of the suture anchor of FIG. 1.
Figure 3:
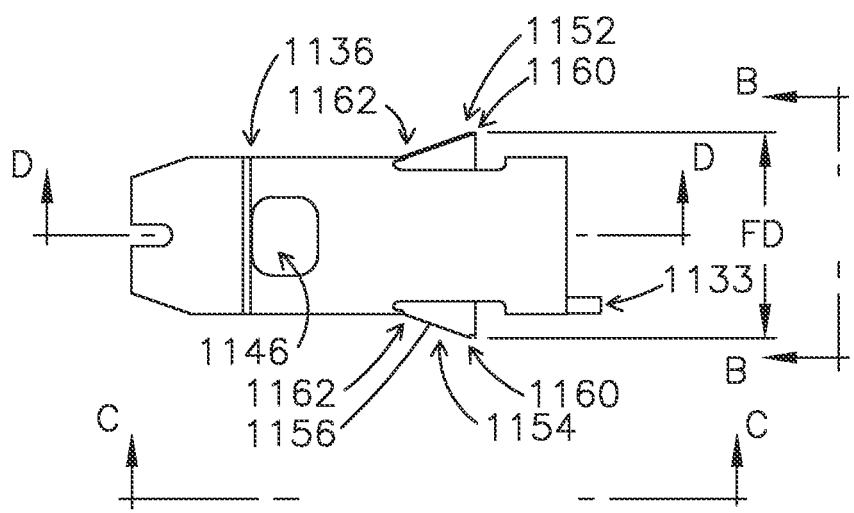
FIG. 3 is a top view of an anchor member for use in an exemplary embodiment of a suture anchor.
Figure 4:
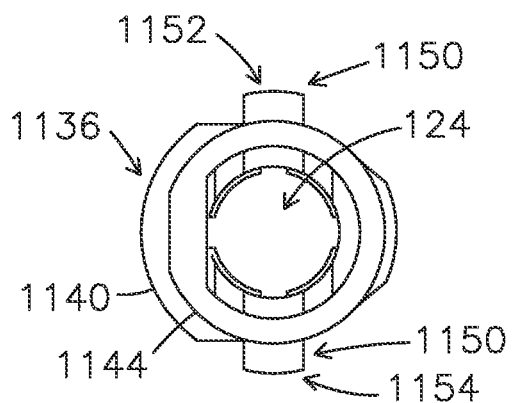
FIG. 4 is a rear view of the anchor member of FIG. 3.
Figure 5:
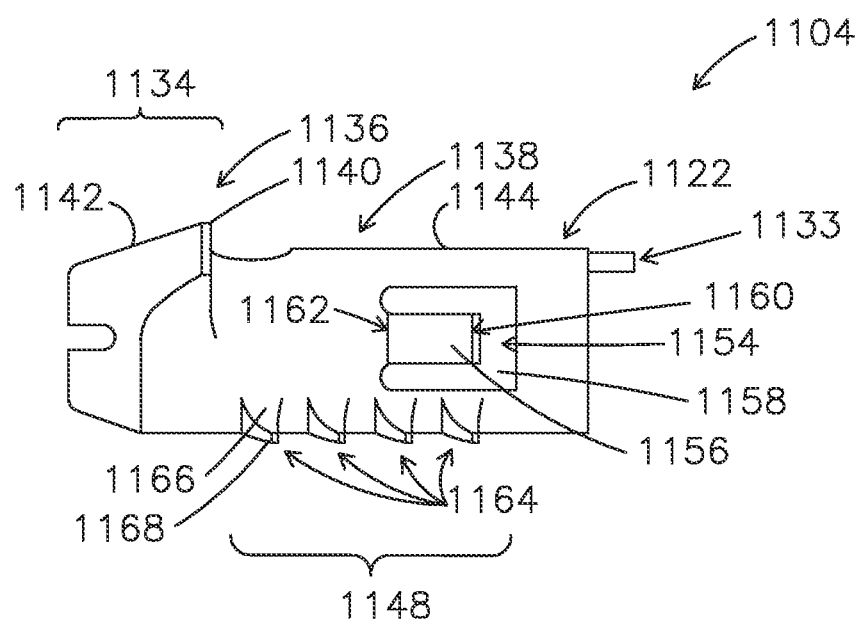
FIG. 5 is a side view of the anchor member of FIG. 3.
Figure 6:
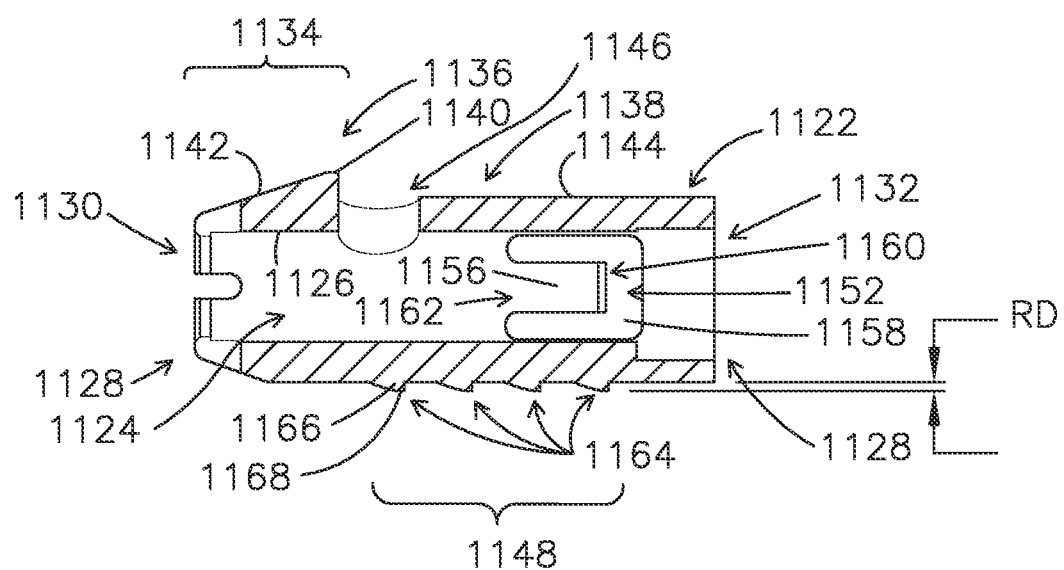
FIG. 6 is a side, cross-section view of the anchor member of FIG. 3.

An exemplary embodiment of a suture anchor 1000 and its components is depicted in FIGS. 1-7 and discussed in detail below. There is shown in FIGS. 1 and 2 that the suture anchor 1000 includes anchor members 1102 illustrated in a suture-unlocked configuration. The anchor members 1102 include an outer anchor member 1104 and an inner anchor member 1106 engaged together to permit relative movement 1108 as between the anchor members 1102 along a longitudinal axis 1110. The suture anchor 1000 also has a distal end 1112 and a proximal end 1114. During implementation the distal end 1112 is positioned further inside a pre-formed hole (e.g., a drilled hole and/or a punched hole) in the bone when the suture anchor 1000 is deployed during the surgical procedure.

The suture anchor 1000 further includes a loading filament 1116 formed with a loop 1118 and legs 1120 that exit the outer anchor member 1104 such as via the proximal end 1114. The loading filament 1116 can be pre-loaded as part of the assembly of the suture anchor 1000. It is also contemplated, however, that the loading filament 1116 can be added before and/or as part of implementation and deployment during the surgical procedure. Each of the loop 1118 and the legs 1120 can be constructed as a contiguous or substantially contiguous piece of material, e.g., wire or suture material. The loop 1118 is generally sized to engage suture material and/or soft tissue such as would be secured to corresponding tissue during the surgical procedure. In one example, suture material is inserted into the loop 1118 and the legs 1120 are manipulated in a manner in which the suture material is drawn into the suture anchor 1000. This action positions the suture material for compression between the anchor members 1102 in the suture-locked configuration (not shown).

With reference to FIGS. 3-6, the outer anchor member 1104 includes an anchor member surface 1122 and a bore 1124 having a bore surface 1126. The bore 1124 has open ends 1128 including an inner anchor member receiving end 1130 and a tool receiving end 1132. Each of the inner anchor member receiving end 1130 and the tool receiving end 1132 are configured to receive therein, respectively, the inner anchor member 1106 and an insertion tool (not shown) or a portion thereof. The outer anchor member 1104 also includes a keying feature 1133 on the tool receiving end 1132 and a step structure 1134 proximate the inner anchor member receiving end 1130. The step structure 1134 forms an upper step feature 1136 and a lower step feature 1138. The upper step feature 1136 includes an outer peripheral surface 1140 and a tapered surface 1142 that extends away from the outer peripheral surface 1140 towards the inner anchor member receiving end 1130.

The lower step feature 1138 includes a lower peripheral surface 1144, located at an offset, the offset being radially inwardly from the outer peripheral surface 1140, and on which is disposed an eyelet opening 1146, a ridged area 1148, and flexible barbs 1150. The flexible barbs 1150 can include a first barb 1152 and a second barb 1154. The flexible barbs 1150 (e.g., the first barb 1152 and the second barb 1154) can be positioned substantially symmetrically about the longitudinal axis 1110 so that one or more of the first barb 1152 and the second barb 1154 can flex in substantially opposing directions. By way of non-limiting example, this flexure can be elastic, wherein each of the first barb 1152 and the second barb 1154 can be compressed radially towards the longitudinal axis 1110, e.g., by a compressive force, and return to its original orientation and/or location upon removal of, e.g., the compressive force.

In the present example, each of the flexible barbs 1150 includes a barb extension 1156 with a shape defined by an aperture 1158 that extends through the lower peripheral surface 1144 to expose a portion of the bore 1124 below. The barb extension 1156 includes a free end 1160 and a pivot end 1162. The latter, i.e., the pivot end 1162, can be formed substantially contiguous with the lower peripheral surface 1144 to permit the flexible barbs 1150 to deflect axially with respect to the longitudinal axis 1110. In one embodiment, a flexure dimension $F_D$ defines the relative position as between the free end 1160 of each of the first barb 1152 and the second barb 1154.

The ridged area 1148 can include one or more ridges 1164. Each of the ridges 1164 has a ridge body 1166 that forms an upper ridge surface 1168 radially offset from the lower peripheral surface 1144 by a ridge dimension $R_D$. The ridge dimension $R_D$ can vary, and in one construction it has a value selected to permit engagement of at least a portion of the ridge body 1166 with, e.g., the cancellous material of the bone. In one example, the ridge body 1166 is likewise configured to extend annularly about the longitudinal axis 1110, thus forming a full or partial arcuate feature on the lower peripheral surface 1144.

The features of the outer anchor member 1104, some of which are discussed above, can be incorporated monolithically such as would occur using manufacturing techniques like molding, casting, and machining. These techniques are likewise suited to form the outer anchor member 1104 as the generally elongated, cylindrical device depicted in FIG. 1.

Alternative shapes with non-circular cross-sections (e.g., elliptical, square, rectangular) are also contemplated for embodying all or a portion of the outer anchor member 1104. Likewise the various features of the outer anchor member 1104 can be configured as one or more separate pieces, which are assembled together using, e.g., fasteners such as adhesives, to form the outer anchor member 1104.

The keying feature 1133 is provided to engage a portion of the actuator tool (not shown) such as by engaging a complementary feature (e.g., a slot) formed on or as part of the actuator tool (not shown). This engagement prevents rotation of the suture anchor 1000 during deployment in the pre-formed hole. The location of the keying feature 1133 can likewise aid in aligning the suture material with parts of the suture anchor 1000 and/or the actuator tool, with one construction of the suture anchor 1000 being configured so that the keying feature 1133 is located on the outer anchor member 1104 by reference (e.g., dimensional reference) to the eyelet opening 1146. Moreover, preventing rotation of the suture anchor 1000 during deployment can help to substantially maintain the alignment of the suture material with corresponding features of the actuator tool such as grooves, openings, slots, and other features that may, e.g., receive the suture material that is secured to the tissue material.

As discussed above and also depicted in FIGS. 3-6, the eyelet opening 1146 can accommodate the loading filament 1116 and/or the suture material that is drawn into and through the eyelet opening 1146 during deployment of the suture anchor 1000. Shapes for the eyelet opening 1146 can include the square and/or rectangular shape illustrated in the appended drawings, as well as other shapes that are sized and configured to permit passage of the filament and/or suture material. Dimensions for the eyelet opening 1146 can vary, with these dimensions in one embodiment of the suture anchor 1000 being selected so as to accommodate at least two strands of suture material.

A benefit of the step structure 1134 is to provide the upper step feature 1136 with features suited to push, plow, or otherwise move material (e.g., cancellous bone material) away from, e.g., the eyelet opening 1146, when the suture anchor 1000 is deployed into the cancellous layer of bone. This "plowing" action can relieve at least some interference and friction that can arise between the bone material and the suture material (or loading filament 1116). Alleviating this interference can permit more accurate tensioning of the suture material, as well as improving control of the desired tension of the suture material, which may be necessary when the suture anchor 1000 is implemented as part of the surgical procedure. In one example, such as the example depicted in FIGS. 3-6, the tapered surface 1142 can be sloped for this purpose. Other constructions of the suture anchor 1000 can incorporate other features on or as part of the tapered surface 1142, these features including, but not limited to, material features such as coatings and deviations disposed on or as part of the tapered surface 1142, all of which can further facilitate the plowing action of the upper step feature 1136.

The upper step feature 1136 can have the generally arcuate shape illustrated in FIGS. 3-6. This shape can describe an angle about the longitudinal axis 1110, in which the angle can define the outer edges of the upper step feature 1136. In one embodiment, this angle can have a value that substantially aligns these outer edges with the outer edges of the eyelet opening 1146. In other embodiments of the suture anchor 1000, the angle can be from about 30° to about 60°, greater than about 180°, and also selected so that the upper step feature 1136 annularly encircles substantially the entire anchor member surface 1122. To avoid removing material of the bone that is proximate the flexible barbs 1150, however, the upper step feature 1136 may include cut-outs, voids, and gaps where material of the upper step feature 1136 is missing so as to limit the amount of material affected, if at all, in front of the flexible barbs 1150 by the plowing action discussed above.

The flexible barbs 1150 can be formed with features suited to engage the bone, e.g., the cancellous material, thus securing the suture anchor 1000 in the bone when deployed during the surgical procedure. The free ends 1160 can each include a proximal face (e.g., the face proximate the proximal end 1114), for example, that extends into and engages the cancellous material in the bone. Different features such as points and barbs, as well as add-on features and devices that facilitate engagement with the bone can also be added to one or more of the flexible barbs 1150 to facilitate this engagement.

Construction of the suture anchor 1000 can take into consideration the thickness of the flexible barbs 1150 and the wall thickness of the outer anchor member 1104. In one embodiment, the suture anchor 1000 can be configured so that the ratio of the thickness of the flexible barbs 1150 relative to the wall thickness of the outer anchor member 1104 is from about 1.2 to about 2, and in one particular construction the ratio is from about 1.5 to about 1.75. In one example, the flexible barbs 1150 can have thickness as measured radially from a surface nearest the longitudinal axis 1110 to the free end 1160 of about 0.04 in and the outer anchor member 1104 can have a wall thickness of about 0.023 in.

Values for the flexure dimension $F_D$ can change between a maximum value in which each of the flexible barbs 1150 (e.g., the first barb 1152 and the second barb 1154) are in their non-flexed position and a minimum value in which all or a portion of the flexible barbs 1150 ingress into the bore 1124. In one embodiment, the suture anchor 1000 is provided wherein the flexure dimension $F_D$ has its maximum value in the undeployed position and/or suture-unlocked configuration. The maximum value can be, for example, just larger than the diameter of bone hole drilled in the bone during the surgical procedure. In one embodiment, the suture anchor 1000 can be constructed so that the maximum value is at least about 20% larger than this diameter. In another embodiment of the suture anchor 1000, the maximum value is from about 10% to about 40% larger than the diameter of the pre-formed hole.

The minimum value of the flexure dimension $F_D$, and the formation of the flexible barbs 1150 generally, can permit ingress of the flexible barbs 1150 into the bore 1124 when the suture anchor 1000 is inserted into the pre-formed hole. This feature is beneficial because it prevents deformation (e.g., notching) of the hole and the corresponding bone material, e.g., by the flexible barbs 1150, during insertion of the suture anchor 1000. By preventing deformation of this bone material, embodiments of the suture anchor 1000 can be more securely fastened or fixated inside of the pre-formed hole, such as by providing more un-disturbed cancellous bone material proximate each of the flexible barbs 1150.

Figure 7:
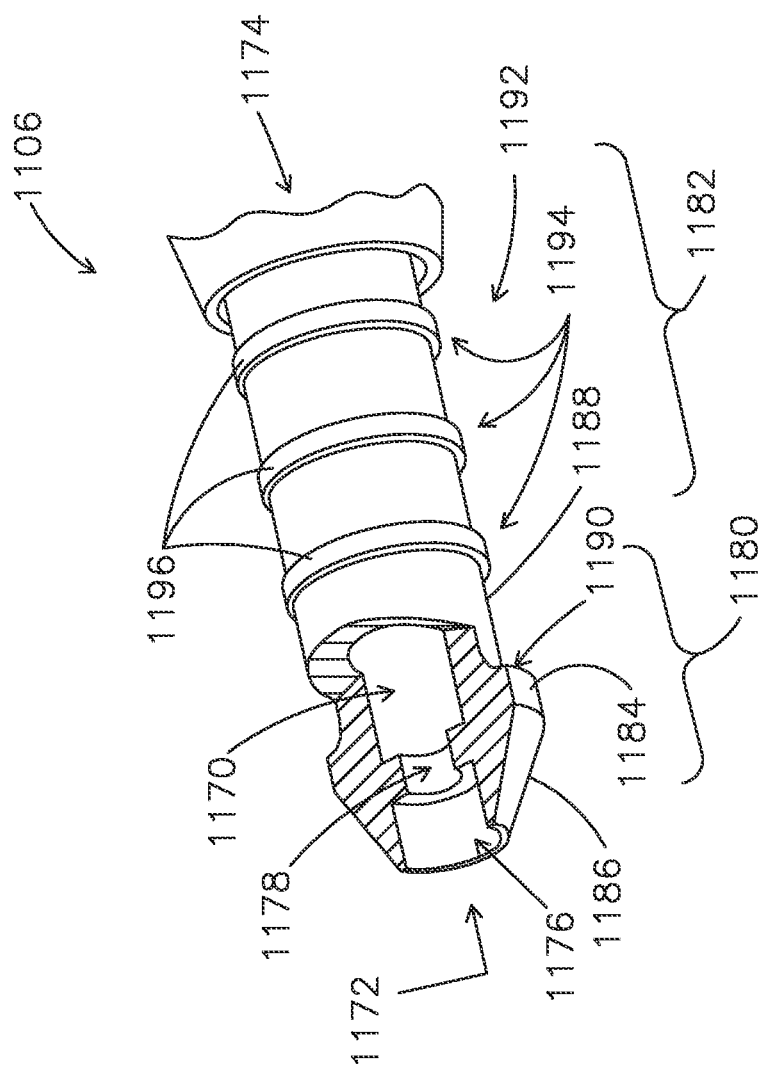
FIG. 7 is a top, perspective, partial cross-section view of another anchor member for use in an exemplary embodiment of a suture anchor.

As depicted in FIG. 7, the inner anchor member 1106 has an inner body bore 1170 that has a forward opening 1172, a rear opening 1174, and an actuator tool engagement region 1176 that forms a reduced diameter region 1178 of the inner body bore 1170. The inner anchor member 1106 also has a distal portion 1180 and a proximal portion 1182. The proximal portion 1182 engages the inner anchor member receiving end 1130 of the outer anchor member 1104 such as by being inserted into the bore 1124 (FIG. 6) of the outer anchor member 1104. The distal portion 1180 includes an outer leading surface 1184 and a tapered leading surface 1186 that extends away from the outer leading surface 1184 towards the forward opening 1172.

In one embodiment, the proximal portion 1182 includes an outer surface 1188, radially inwardly offset from the outer leading surface 1184 to form a shoulder 1190. A securing feature 1192 can be disposed on the outer surface 1188, the securing feature 1192 working in conjunction with the bore surface 1126 of the outer anchor member 1104 to secure the suture material in the suture-locked configuration. The securing feature 1192 includes a plurality of projections 1194 that form an engagement surface 1196. In the present example, the engagement surface 1196 is positioned in radial offset from the outer surface 1188, and at least a portion of the engagement surface 1196 can likewise extend annularly about the longitudinal axis 1110.

As discussed in connection with the outer anchor member 1104 above, the inner anchor member 1106 and its associated features can be formed monolithically using known manufacturing techniques, as well as in one or more separate pieces that are assembled together. In one embodiment, the inner anchor member 1106 can form the elongated cylindrical shape illustrated in FIG. 7. The diameter of such shape can vary, with the construction of the shape that forms the projections 1194, and more particularly the engagement surface 1196, being configured with a diameter that causes compression of the suture material between the engagement surface 1196 and the bore surface 1126. This compression can occur when the suture anchor 1000 is in the suture-locked configuration. The amount of compression can be defined by a compression ratio of the suture material, which can be greater than about 1.5:1. In one example, the compression ratio is from about 2:1 to about 2.5:1.

The radial offset of the engagement surface 1196 from the outer surface 1188 can likewise improve and/or facilitate fixation of the suture material in the suture anchor 1000 when in the suture-locked configuration. In one embodiment, the value for the radial offset can be selected to create a tortuous path as between the outer surface 1188 and the bore surface 1126. The suture material can pass through the tortuous path, with compression of the suture member occurring at compression points formed between the engagement surface 1196 and the bore surface 1126.

The actuator tool engagement region 1176 can be configured to engage the actuator tool (not shown) so that the actuator tool can change the suture anchor 1000 between the suture-unlocked configuration and the suture-locked configuration. In one embodiment, the reduced diameter region 1178 is sized and configured to form shearable features, e.g., stepped surfaces, which fit corresponding features on the insertion tool. These shearable features can disengage from the inner anchor member 1106 such as from the inner body bore 1170. In one embodiment, disengagement of the material forming the shearable features occurs when the suture anchor 1000 is placed in its suture-locked configuration. The shearable features are thereafter removed such as by removing the insertion tool from the pre-formed hole.

Figure 8:
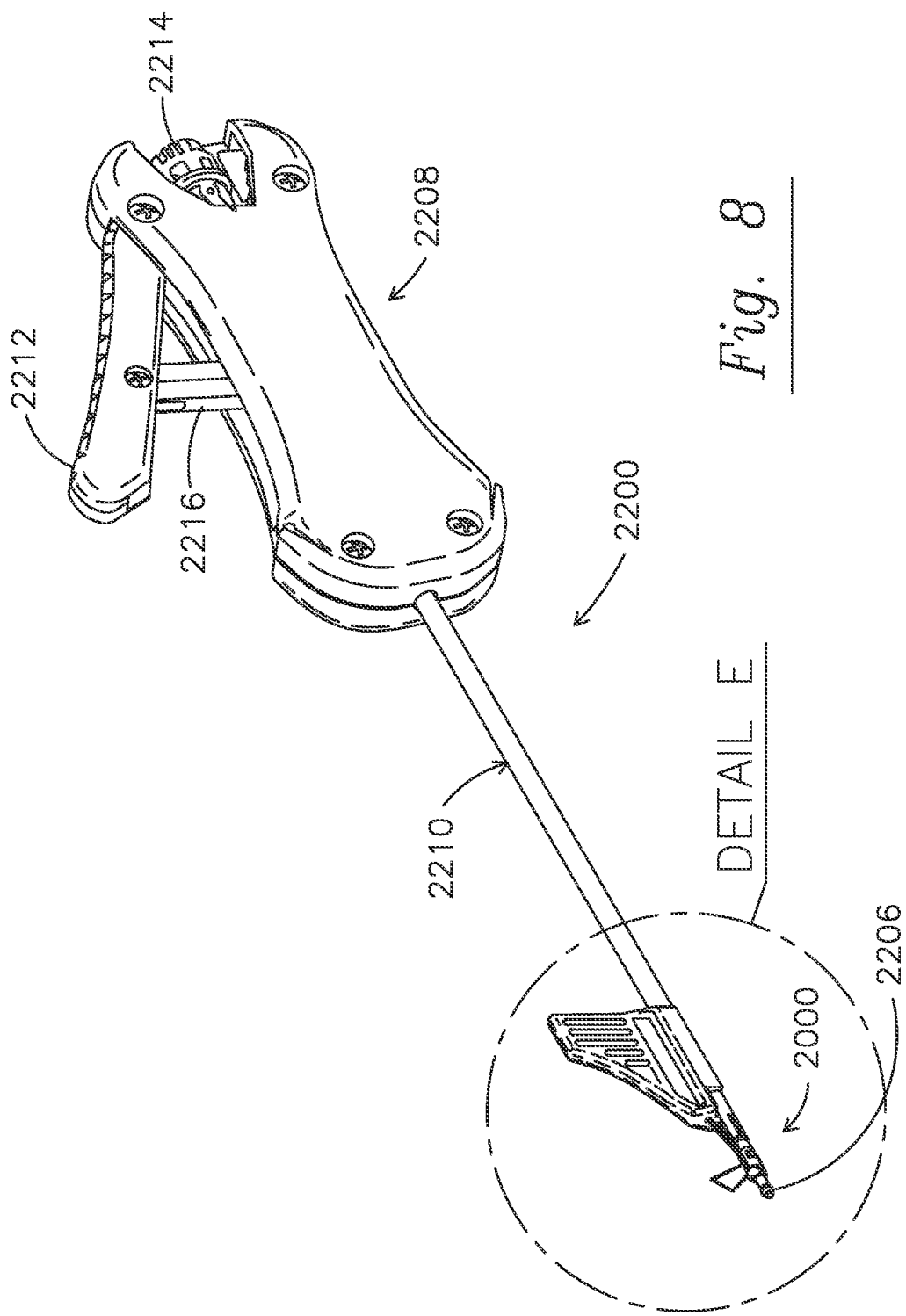
FIG. 8 is a top, perspective view of a suture anchor system.
Figure 9:
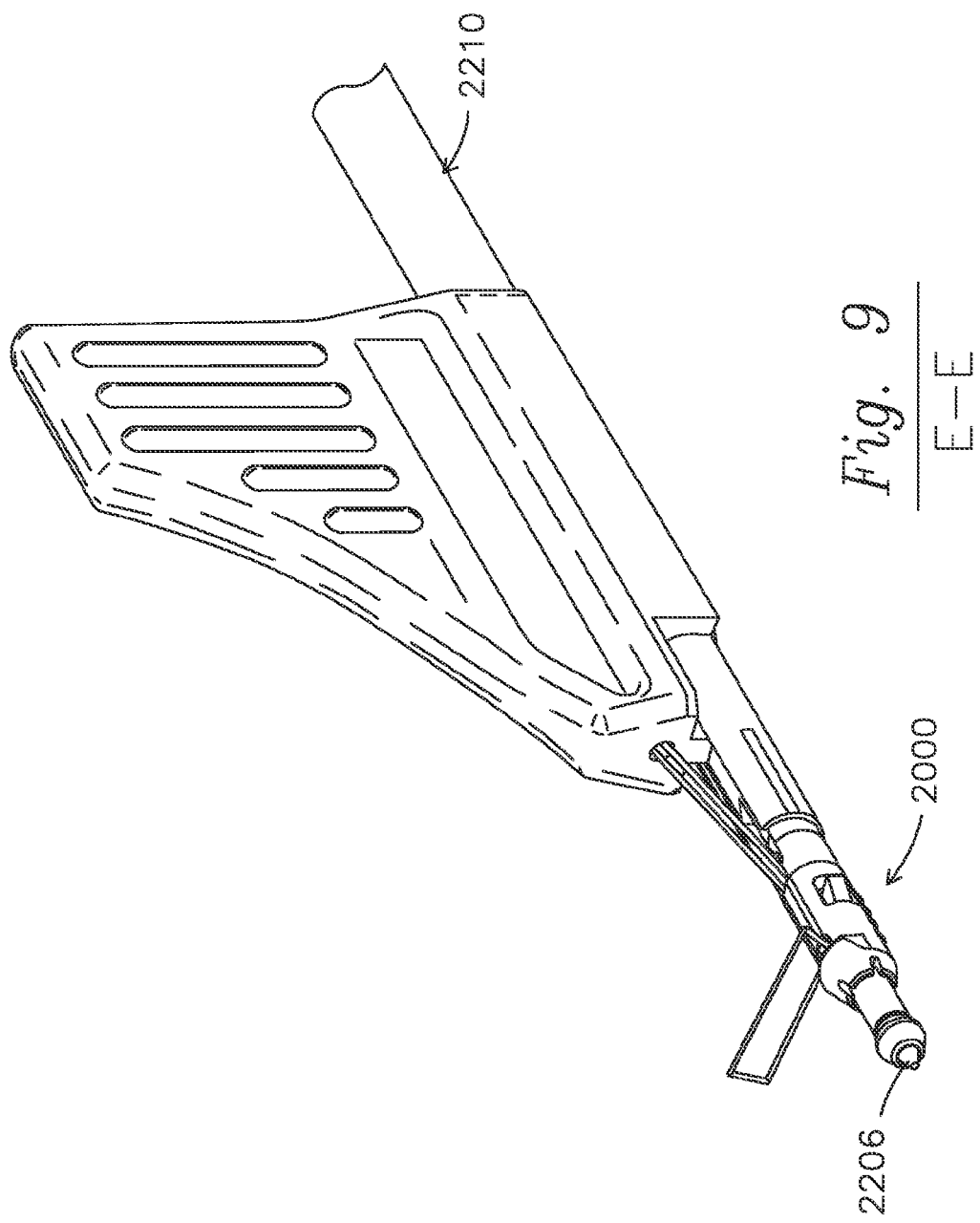
FIG. 9 is a top, perspective, detail view of the suture anchor system of FIG. 8.

To further clarify these and other features, and discussing generally some implementations of suture anchors such as the suture anchor 1000 discussed above, reference can now be had to FIGS. 8 and 9, in which there is illustrated one implementation of an exemplary embodiment of a suture anchor 2000. Where applicable like numerals are used to identify like components as between FIGS. 1-7 and FIGS. 8 and 9, but the numerals are increased by 1000 (e.g., 1000 is now 2000 in FIG. 8). As depicted in FIGS. 8 and 9, the suture anchor 2000 is situated on an actuator tool 2200 that has a distal end 2202 and a proximal end 2204. More particularly, the suture anchor 2000 is positioned on the proximal end 2204 so as to engage a mandrel 2206, the mandrel 2206 being provided to actuate the suture anchor 2000 between its suture-locked and suture-unlocked configurations. The actuator tool 2200 further includes a handle 2208 and an elongated shaft 2210 that houses the mandrel 2206 therein.

The operation of the actuator tool 2200, and the general steps of its implementation during a surgical procedure, are performed when the user has properly passed the suture material through the target tissue and the loop 1118 (FIGS. 1 and 2), inserted the suture anchor 2000 into the pre-formed hole in the bone, and applied sufficient tension to the suture material so as to justify deploying the suture anchor 2000. Additional details regarding the method of using suture anchors such as the suture anchor 1000 and 2000 may be had by reference to the aforementioned patent application. Such deployment knotlessly secures the suture material (or tissue) to the bone. In one example, the actuator tool comprises a trigger 2212, a knob 2214, a safety latch 2216, and a drive mechanism (not shown). The drive mechanism, while not shown in the appended drawings, can include levers, pivots, rollers, joints, and other mechanisms that are arranged together to provide longitudinal movement of the mandrel 2206. This longitudinal movement causes the relative movement of the parts of the suture anchor 2000 (e.g., the outer anchor member 1104 and the inner anchor member 1106) as discussed in detail above, and in one example the configuration of the suture anchor 2000 changes from the suture-unlocked configuration to the suture locked configuration.

Referring next to FIGS. 10-15, there is illustrated some implementations of suture anchors made in accordance with concepts of the present invention. Again where applicable, like numerals are used to identify like components as between the FIGS. 1-7 and 10-15, except the numerals are increased by 2000 (e.g., 1000 is now 3000). Moreover, whereas the FIGS. 10-15 illustrate exemplary embodiments of suture anchors contemplated herein, it is recognized that these embodiments may or may not illustrate all of the features found, e.g., in the suture anchor 1000 and 2000 illustrated and described above. The absence of these features does not, however, limit the scope or spirit of the present disclosure or the embodiments of the suture anchors disclosed and described herein. Any and all of the features discussed in connection with the other embodiments in the present disclosure are likewise applicable to any other embodiments, including those embodiments illustrated in FIGS. 10-15 and described below.

Figure 10:
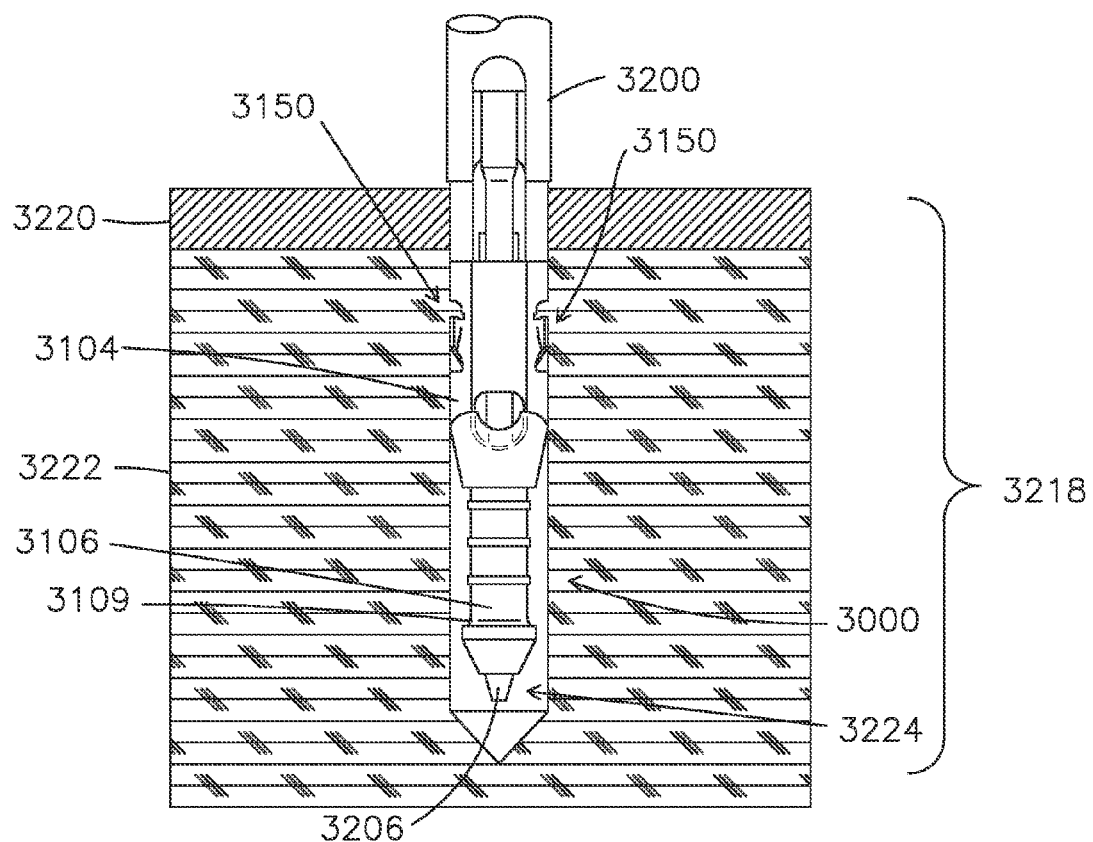
FIG. 10 is a side view of an exemplary embodiment of a suture anchor implemented in a suture-unlocked configuration during a surgical procedure.
Figure 11:
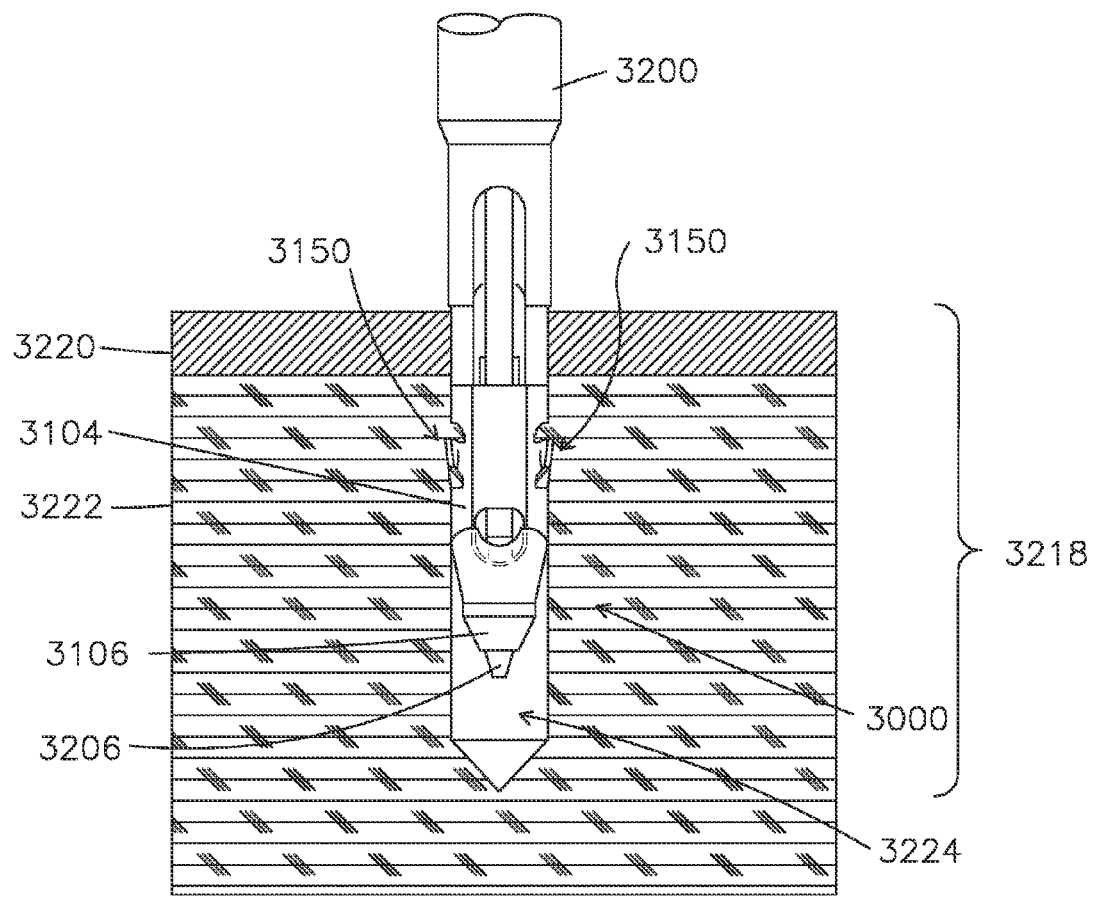
FIG. 11 is a side view of the suture anchor of FIG. 10 in a suture-locked configuration.

Referring now to FIGS. 10 and 11, there is depicted one implementation of an exemplary embodiment of a suture anchor 3000 in its suture-unlocked configuration (FIG. 10) and suture-locked configuration (FIG. 11). In the present example, the suture anchor 3000 is attached to an actuator tool 3200, and more particularly the suture anchor 3000 is coupled to a mandrel 3206. Suture material has been omitted for clarity. The suture anchor 3000 is found in a bone 3218 with an upper cortical layer 3220 and a lower cancellous layer 3222. A pre-formed hole 3224 is provided into which the suture anchor 3000 is positioned for deployment as part of the surgical process.

In FIG. 10, it is noted that insertion of the suture anchor 3000 into the pre-formed hole 3224 causes each of the flexible barbs 3150 to flex radially inward so as to reduce the flexure dimension $F_D$. This prevents notching of the sides and surfaces of, e.g., the pre-formed hole 3224, and also permits the suture anchor 3000 to be positioned inside of the pre-formed hole 3224 at a sufficient depth to be readied for deployment. Deployment occurs when the actuator tool 3200 is activated to cause the mandrel 3206 to move towards the actuator tool 3200. This movement pulls the inner anchor member 3106 upward, towards the upper cortical layer 3220, until the shoulder 3190 is seated against one or more surfaces proximate the inner anchor member receiving end 3130 of the outer anchor member 3104. Movement of the outer anchor member 3104 can be prevented in one respect by ridges (e.g., ridges 1164) disposed on the outer anchor member 3104.

Movement of the inner anchor member 3106 can cause the flexible barbs 3150 to move radially outwardly into engagement with the material of the lower cancellous layer 3222. This movement can also change the value of the flexure dimension $F_D$, and more particularly the change in the value can occur due to interference between the inner anchor member 3106 and portions of the flexible barbs 3150. This interference can maintain the value of the flexure dimension $F_D$, and in one construction the anchor members are configured so that this interference prevents any further movement of the flexible barbs towards the longitudinal axis. As depicted in FIG. 10, in one example the interference at the final seated position of the shoulder 3190 against the inner anchor member receiving end 3130 causes the maximum value of the flexure dimension $F_D$. This maximum value secures the suture anchor 3000 in its suture-locked configuration.

Figure 12:
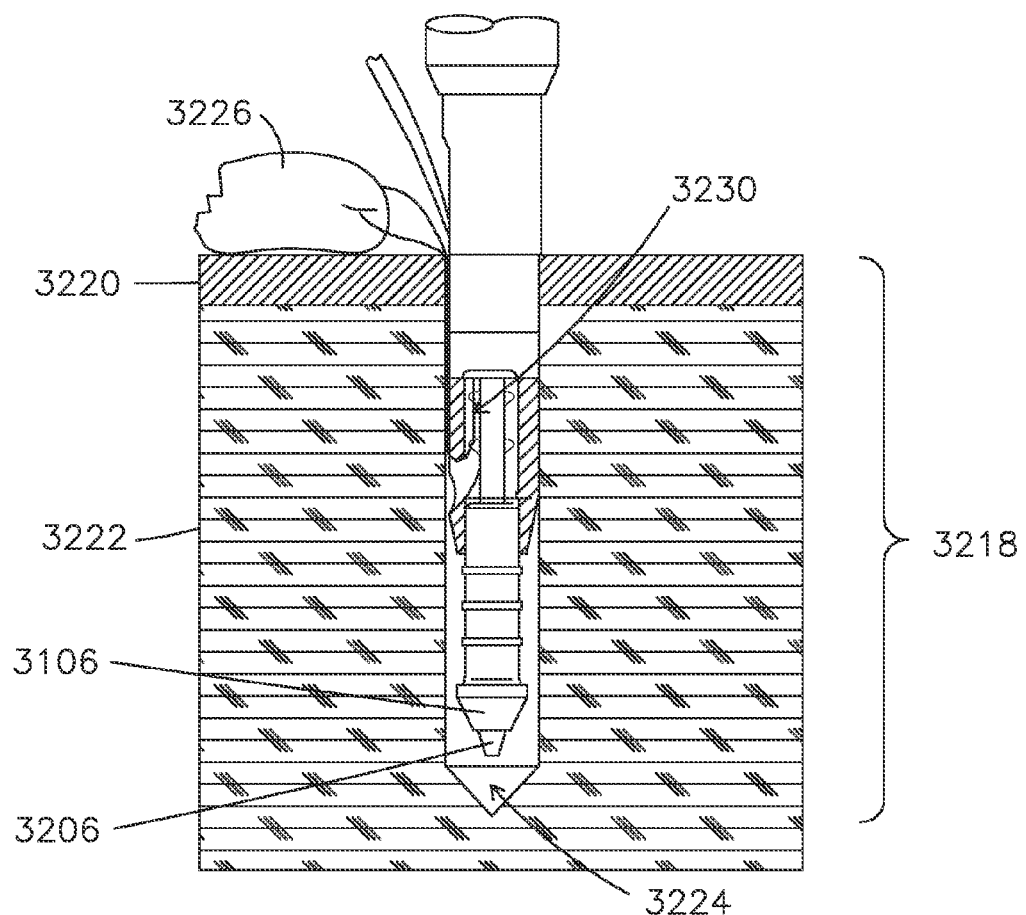
FIG. 12 is a side view of an exemplary embodiment of a suture anchor implemented in a suture-unlocked configuration during a surgical procedure.
Figure 13:
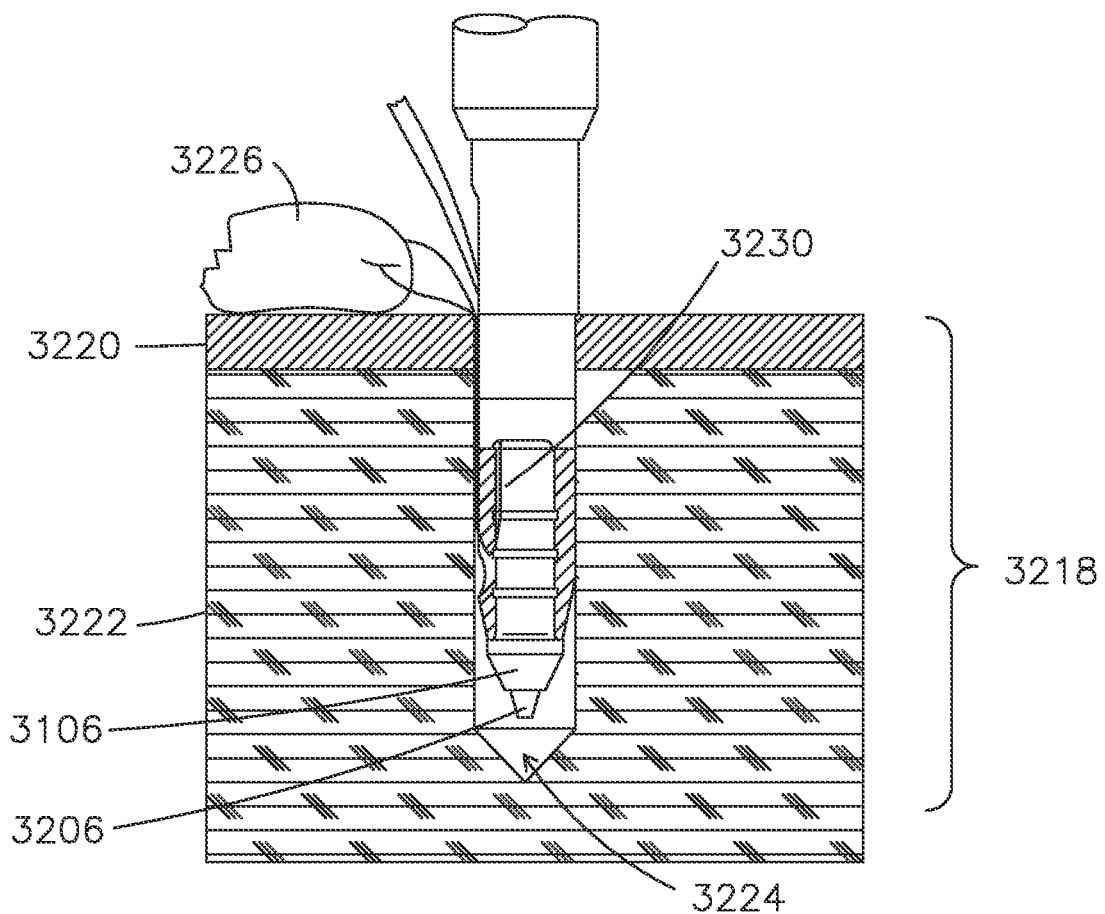
FIG. 13 is a side view of the suture anchor of FIG. 12 in a suture-locked configuration.

Another implementation of the suture anchor 3000 is illustrated in FIGS. 12 and 13 and described below. In FIG. 12, the suture anchor 3000 is shown in its suture-unlocked configuration. There is also illustrated a tissue 3226 and suture material 3228, which is attached to the tissue 3226 and drawn into the suture anchor 3000. In FIG. 13, the suture anchor 3000 is illustrated in its suture-locked configuration in which a tortuous path 3230 is formed as between the inner anchor member 3106 and the outer anchor member 3104. The suture material 3228 is found in at least a portion of the tortuous path 3230 further fixating the suture material in the suture anchor 3000.

Figure 14:
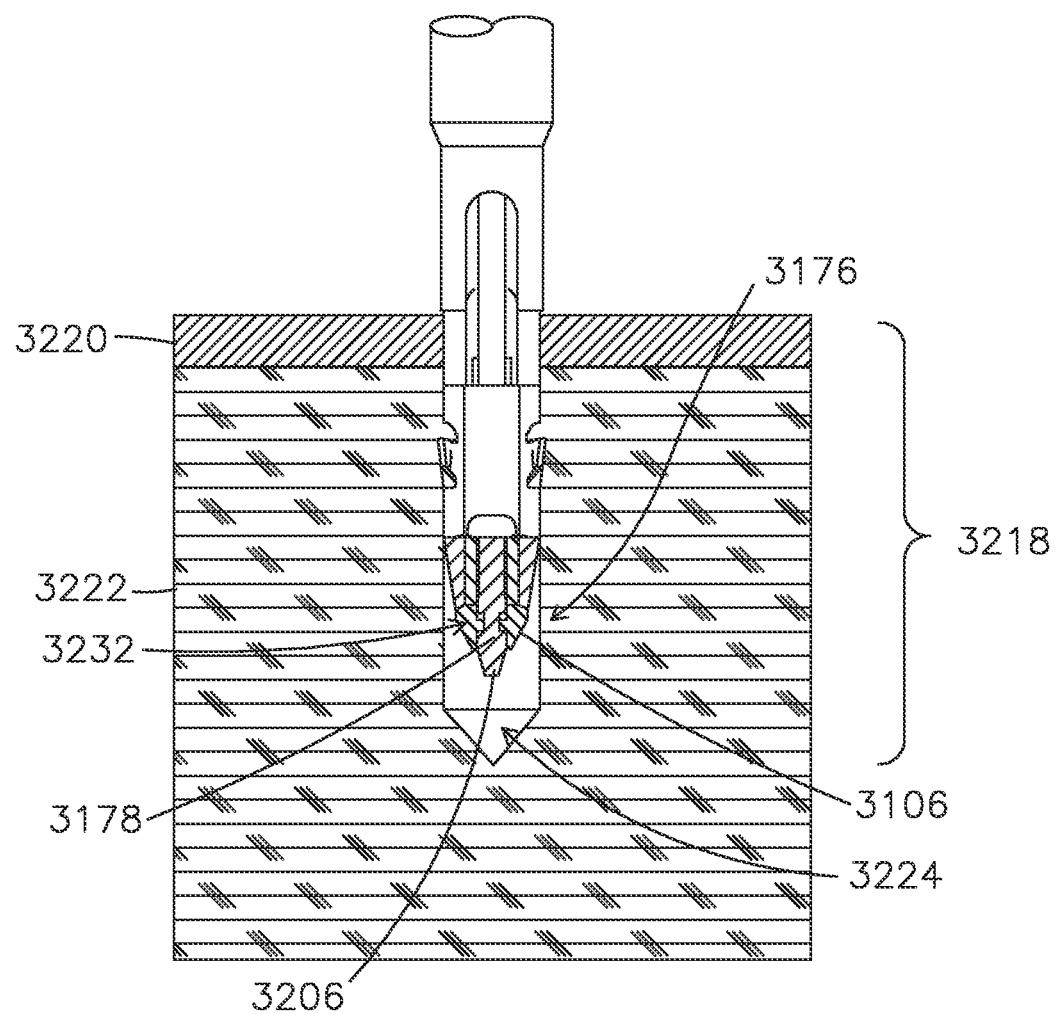
FIG. 14 is a side view of an exemplary embodiment of a suture anchor implemented in a suture-unlocked configuration during a surgical procedure.
Figure 15:
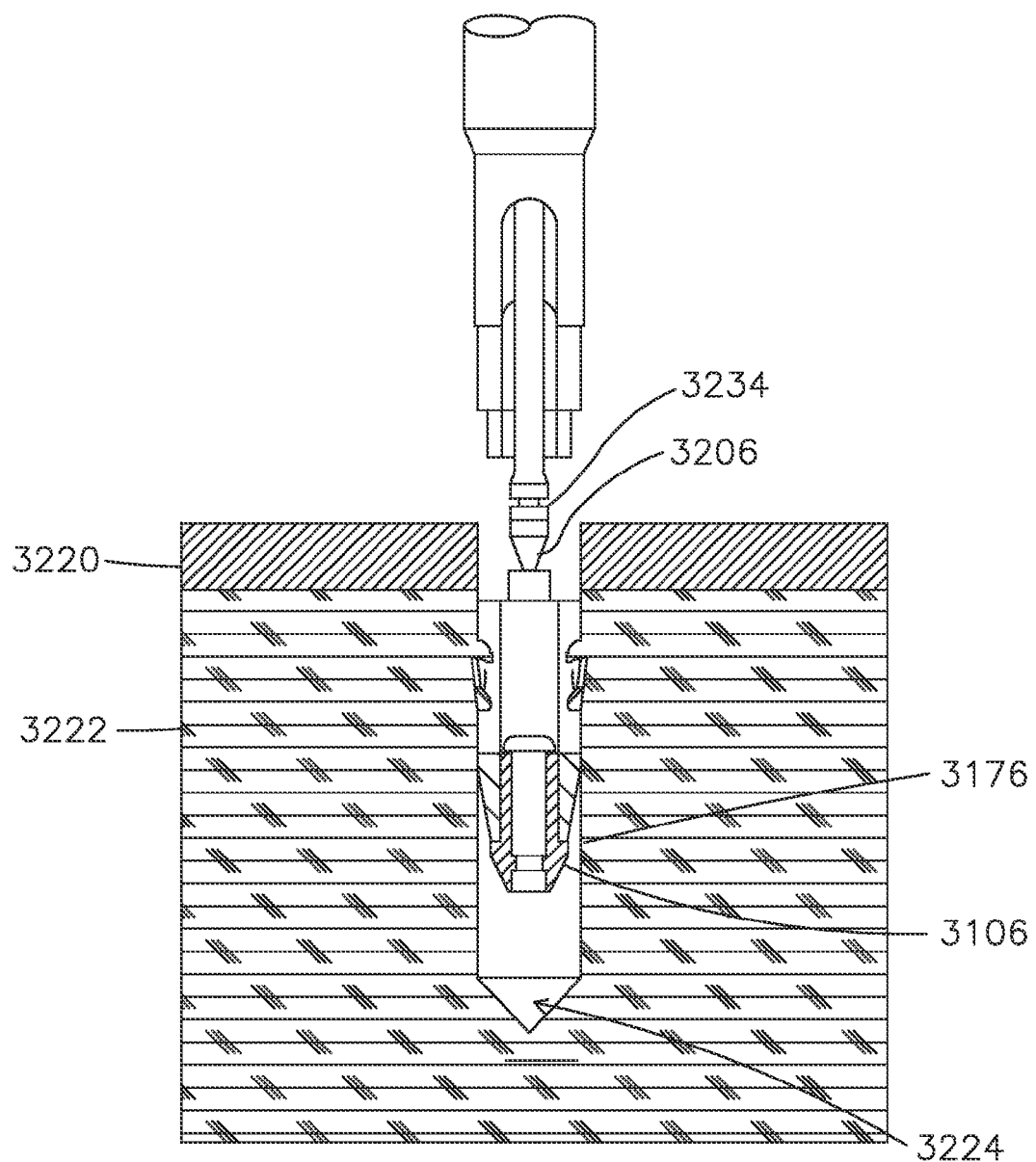
FIG. 15 is a side view of the suture anchor of FIG. 14 in a suture-locked configuration.

Yet another implementation of the suture anchor 3000 is shown in FIGS. 14 and 15, in which there is depicted an example of the engagement between the mandrel 3206 and the actuator tool engagement region 3176 of the inner anchor member 3106. The actuator tool engagement region 3176 includes a shearable connection 3232 formed between the reduced diameter region 3178 and a portion of the mandrel 3206. In one example, the mandrel 3206 may include features corresponding to the size, shape, configuration, and dimensions of the reduced diameter region 3178. As illustrated in FIG. 15, further actuation of the actuator tool 3200 can cause shearing of the shearable connection 3232 so as to release the mandrel 3206 from the suture anchor 3000. In one example, portions of the inner anchor member 3106 such as material 3234 proximate the reduced diameter region 3178 may be found on the mandrel 3206 when it is extricated from the suture anchor 3000.

Figure 16:
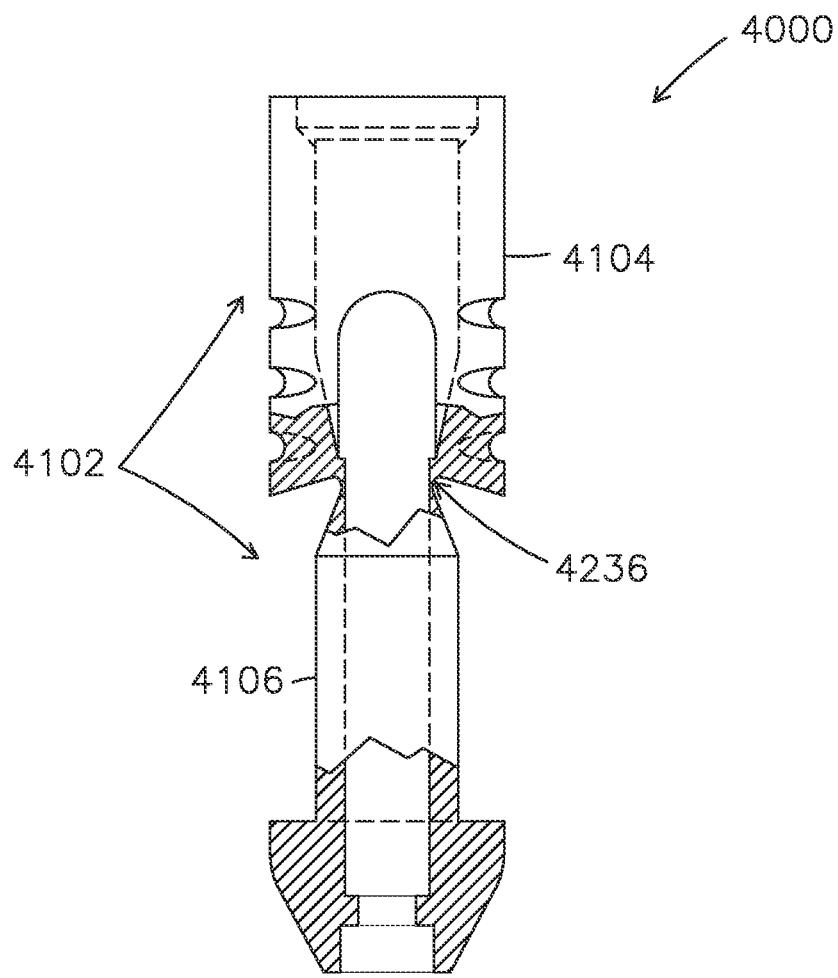
FIG. 16 is a side, partial cross-section view of an exemplary embodiment of a suture anchor.

Additional shearable connections can secure the outer anchor member and the inner anchor member such as by way of manufacturing of the suture anchor. For example, and with reference to FIG. 16, there is illustrated another exemplary embodiment of a suture anchor 4000 made in accordance with concepts of the present invention. In this embodiment, the suture anchor 4000 comprises anchor members 4102, and more particular to this example the anchor members 4102 include an outer anchor member 4104 and an inner anchor member 4106 that are secured together with a shearable connection 4236. When deployed in the pre-formed hole, movement of the mandrel (not shown) can fracture the shearable connection 4236. This fracture permits the relative movement of the outer anchor member 4104 and the inner anchor member 4106. This movement can lead to the final positioning of the anchor members 4102 in the suture-locked configuration details of which are described above.

Figure 17:
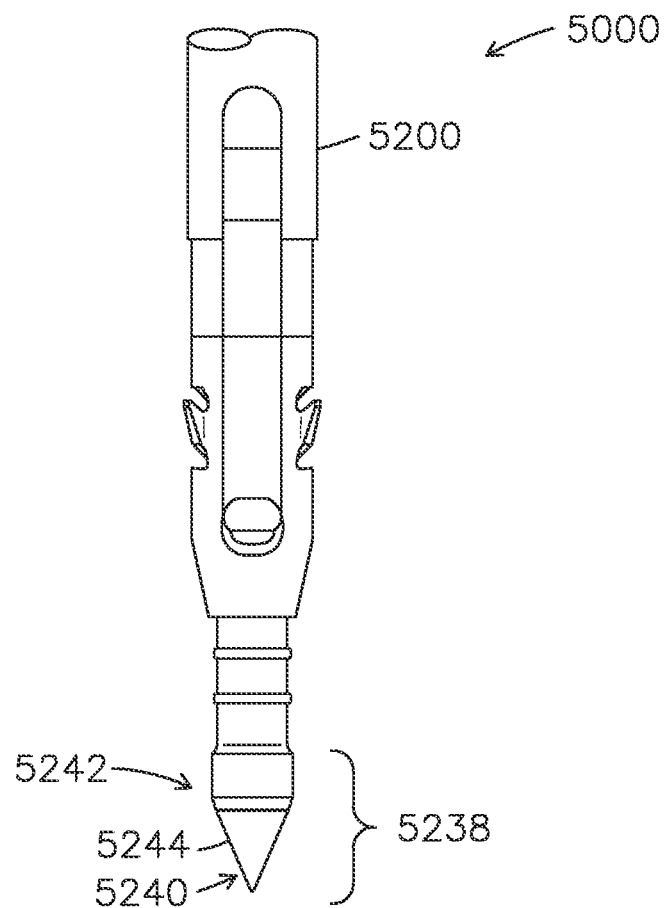
FIG. 17 is a side view of an exemplary embodiment of a suture anchor.

Still another embodiment of a suture anchor 5000 is illustrated in FIG. 17. In this embodiment, the mandrel 5206 of the actuator tool 5200 is provided with a puncturing feature 5238. This puncturing feature 5238 includes distal tip portion 5240, a proximal tip portion 5242 adjacent the distal portion 5180 of the inner anchor member 5106, and a substantially conical surface 5244 there between. The distal tip portion 5240 is configured to puncture bone material, such as the bone 3218 (FIG. 10), the upper cortical layer 3220 (FIG. 10), and the lower cancellous layer 3222 (FIG. 10). This feature is beneficial because it can eliminate the need for the pre-formed hole (e.g., the pre-formed hole 3224 (FIG. 10)).

It is contemplated that numerical values, as well as other values that are recited herein are modified by the term "about", whether expressly stated or inherently derived by the discussion of the present disclosure. As used herein, the term "about" defines the numerical boundaries of the modified values so as to include, but not be limited to, tolerances and values up to, and including the numerical value so modified. That is, numerical values can include the actual value that is expressly stated, as well as other values that are, or can be, the decimal, fractional, or other multiple of the actual value indicated, and/or described in the disclosure.

While the present invention has been particularly shown and described with reference to certain exemplary embodiments, it will be understood by one skilled in the art that various changes in detail may be effected therein without departing from the spirit and scope of the invention as defined by claims that can be supported by the written description and drawings. Further, where exemplary embodiments are described with reference to a certain number of elements it will be understood that the exemplary embodiments can be practiced utilizing either less than or more than the certain number of elements.

What is claimed is:

1. A suture anchor for securing suture material to bone, said suture anchor comprising:
    an outer anchor member having a bore surface defining a bore extending from a distal end to a proximal end along a longitudinal axis;
    an inner anchor member moveable within the bore between a suture-unlocked configuration and a suture-locked configuration, the inner anchor member including an actuator tool engagement region configured to engage a mandrel to pass a force required to move the inner anchor member from the suture-unlocked configuration to the suture-locked configuration;
    two apertures extending through the outer anchor member from an outer surface of the outer anchor member to the bore such that the apertures oppose one another across the longitudinal axis;
    an upper step feature disposed on the outer anchor member, the upper step feature comprising a tapered surface sloping from the distal end to an outer peripheral surface;
    a lower step feature including a lower peripheral surface located on an offset being radially inward from the outer peripheral surface;
    an eyelet opening positioned proximal the upper step feature and on the lower step feature, the eyelet opening extending through the outer anchor member in a manner exposing the bore, the eyelet opening being configured to accommodate at least two strands of the suture material,
    a securing feature disposed on an outer surface of the inner anchor member, the securing feature configured to compress the suture material against the bore surface when the inner anchor member is in the suture-locked configuration; and two flexible barbs disposed on the outer anchor member, each of the flexible barbs being hinged from a distal extent thereof to a distal wall of a respective one of the two apertures, the flexible barbs being elastically compressible to a first dimension in the suture-unlocked configuration and the flexible barbs being maintained to a second dimension in the suture-locked configuration, wherein the first dimension is smaller than the second dimension, wherein said upper step feature comprises a generally arcuate shape describing an angle about the longitudinal axis, the angle being limited such that the upper step feature is missing distal to and proximate the two flexible barbs.

2. The suture anchor according to claim 1 further comprising a keying feature disposed on the distal end of the outer anchor member, wherein the keying feature comprises a feature that couples the outer anchor member with an actuator tool housing the mandrel, and wherein the feature prevents rotation of the outer anchor member independent of the actuator tool.

3. The suture anchor according to claim 1, wherein the securing feature comprises a plurality of projections forming an engagement surface that has an offset that is radially outward from the outer surface of the inner anchor member, and wherein the engagement surface causes compression of the suture material against the bore surface when the inner anchor member is in the suture-locked configuration.

4. The suture anchor according to claim 1, wherein the two flexible barbs consist of a first barb and a second barb formed symmetrically about the longitudinal axis so that the first barb and the second barb flex in opposing directions.

5. The suture anchor according to claim 1, wherein the actuator tool engagement region includes a shearable feature coupled to the mandrel.

6. The suture anchor according to claim 5, wherein the shearable feature includes a reduced diameter region forming a stepped feature configured to engage a complementary feature on the mandrel.

7. The suture anchor according to claim 1, further comprising one or more of a loading filament and suture material passing through at least a portion of the bore.

8. The suture anchor according to claim 1, wherein each of the flexible barbs is elastically compressible from a natural state dimension to the first dimension in the suture-unlocked configuration, the natural state dimension being similar to the second dimension.

9. A suture anchor for knotless securing of tissue material to bone, said suture anchor comprising:

an outer anchor member comprising a bore having an inner anchor member receiving end, a tool receiving end, a bore surface extending along a longitudinal axis therebetween, a first aperture and a second aperture arranged to oppose the first aperture across the longitudinal axis;

an inner anchor member moveable within the bore between a suture-unlocked configuration and a suture-locked configuration, the inner anchor member having an inner body bore extending along the longitudinal axis, the inner body bore for receiving a mandrel of an insertion tool configured to cause a force required to move the inner anchor member from the suture-unlocked configuration to the suture-locked configuration;

a reduced diameter region formed in the inner body bore, the reduced diameter region being shearable by the mandrel;

an engagement surface disposed on the inner anchor member, the engagement surface configured to compress suture material against the bore surface in the suture-locked configuration;

an eyelet opening extending through the outer anchor member exposing the bore;

an upper step feature between the eyelet opening and a distal end of the outer anchor member, the upper step feature forming an outer peripheral surface and a tapered surface sloping from the outer peripheral surface toward the distal end;

a lower step feature including a lower peripheral surface located on an offset being radially inward from the outer peripheral surface; and flexible barbs disposed on the outer anchor member, the flexible barbs comprising a first barb hinged to a distal extent of the first aperture and a second barb hinged to a distal extent of the second aperture while being formed symmetrically about the longitudinal axis so that the first barb and the second barb move in radially opposing directions during installation in a hole in the bone, each of the first barb and the second barb having a free end that is elastically moveable to a first position in the suture-unlocked configuration and the free end being maintained to a second position in the suture-locked configuration, wherein the first position is smaller than the second position, wherein said upper step feature comprises a generally arcuate shape describing an angle about the longitudinal axis, the angle being limited such that the upper step feature is missing distal to and proximate the flexible barbs, and wherein the eyelet opening is positioned on the lower step feature.

10. The suture anchor according to claim 9 further comprising a plurality of projections disposed on an outer surface of the inner anchor member, wherein each of the projections is positioned on the engagement surface with an offset that is radially outward from the outer surface.

11. The suture anchor according to claim 9 further comprising a plurality of ridges disposed on the outer anchor member, wherein the ridges are positioned on the outer anchor member opposite the upper step feature.

12. The suture anchor according to claim 9, wherein the upper step feature has the generally arcuate shape with outer edges aligned with outer edges of the eyelet opening.

13. The suture anchor according to claim 9, wherein each of the flexible barbs is elastically compressible from a natural state position to the first position in the suture-unlocked configuration, the natural state position being similar to the second position.

* * * * *